United States Patent [19]

Wright

[11] Patent Number: 5,792,749

[45] Date of Patent: Aug. 11, 1998

US005792749A

[54] METHOD AND COMPOSITION FOR LOWERING LOW DENSITY LIPOPROTEIN CHOLESTEROL

[75] Inventor: H. Tonie Wright, Richmond, Va.

[73] Assignee: Virginia Commonwealth University, Richmond, Va.

[21] Appl. No.: 781,020

[22] Filed: Jan. 9, 1997

[51] Int. Cl.[6] .................. A61K 38/00; A61K 38/16; C07K 14/00
[52] U.S. Cl. .................. 514/12; 514/824; 530/324
[58] Field of Search .................. 514/12; 530/324

[56] References Cited

U.S. PATENT DOCUMENTS

| | | | |
|---|---|---|---|
| 5,175,253 | 12/1992 | Fallon et al. | 530/330 |
| 5,514,653 | 5/1996 | Perlmutter et al. | 514/12 |
| 5,604,201 | 2/1997 | Thomas et al. | 514/12 |
| 5,668,107 | 9/1997 | Miller et al. | 514/12 |

*Primary Examiner*—Cecilia J. Tsang
*Assistant Examiner*—Michael Borin
*Attorney, Agent, or Firm*—Whitham, Curtis & Whitham

[57] ABSTRACT

$\alpha_1$-antitrypsin and peptide fragments and derivatives thereof are used to upregulate low density lipoprotein (LDL) cholesterol receptor levels and increase bile acid synthesis in the liver, and this results in a decrease in circulating LDL cholesterol levels in the patient's circulatory system.

6 Claims, 7 Drawing Sheets

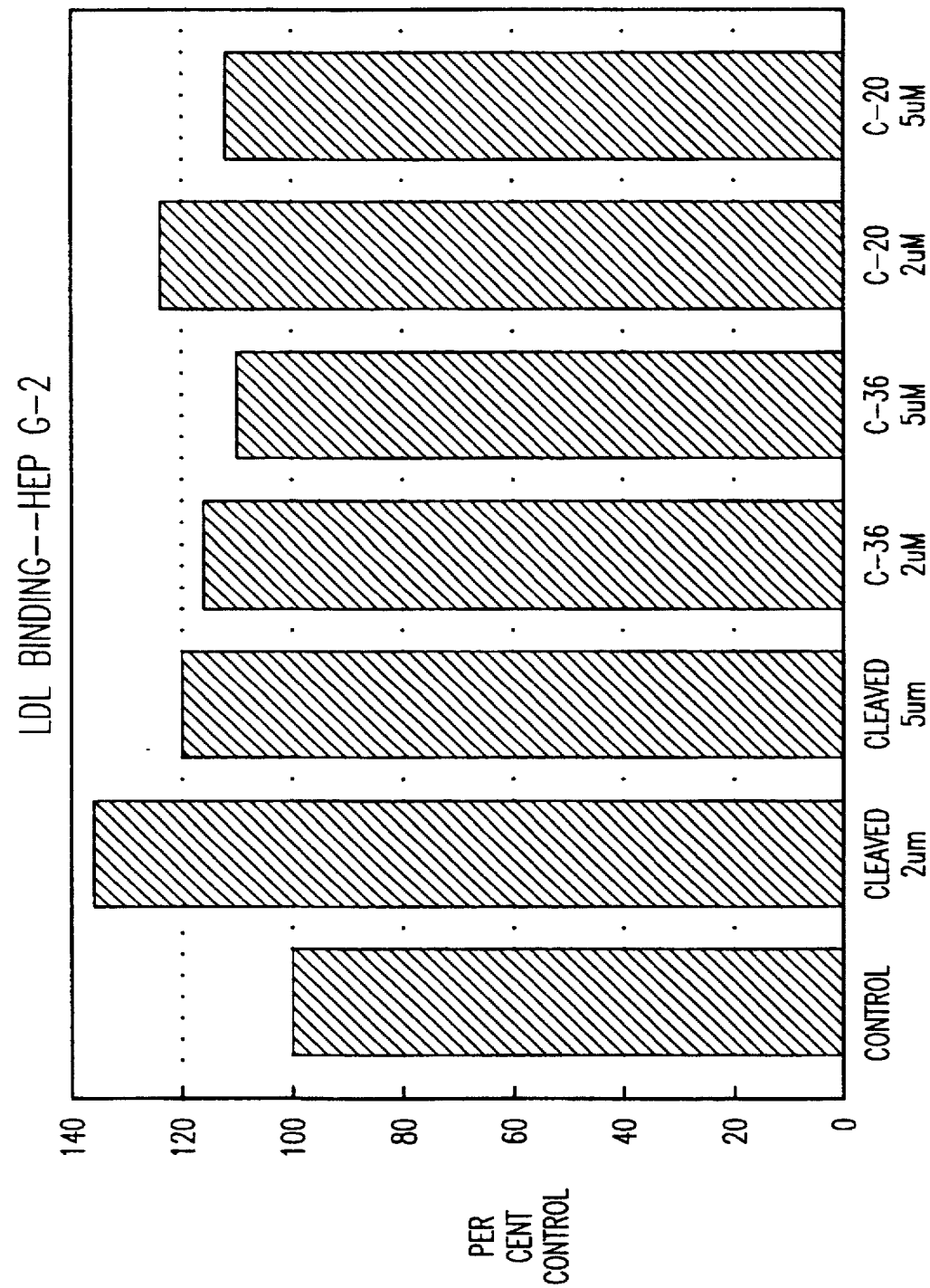

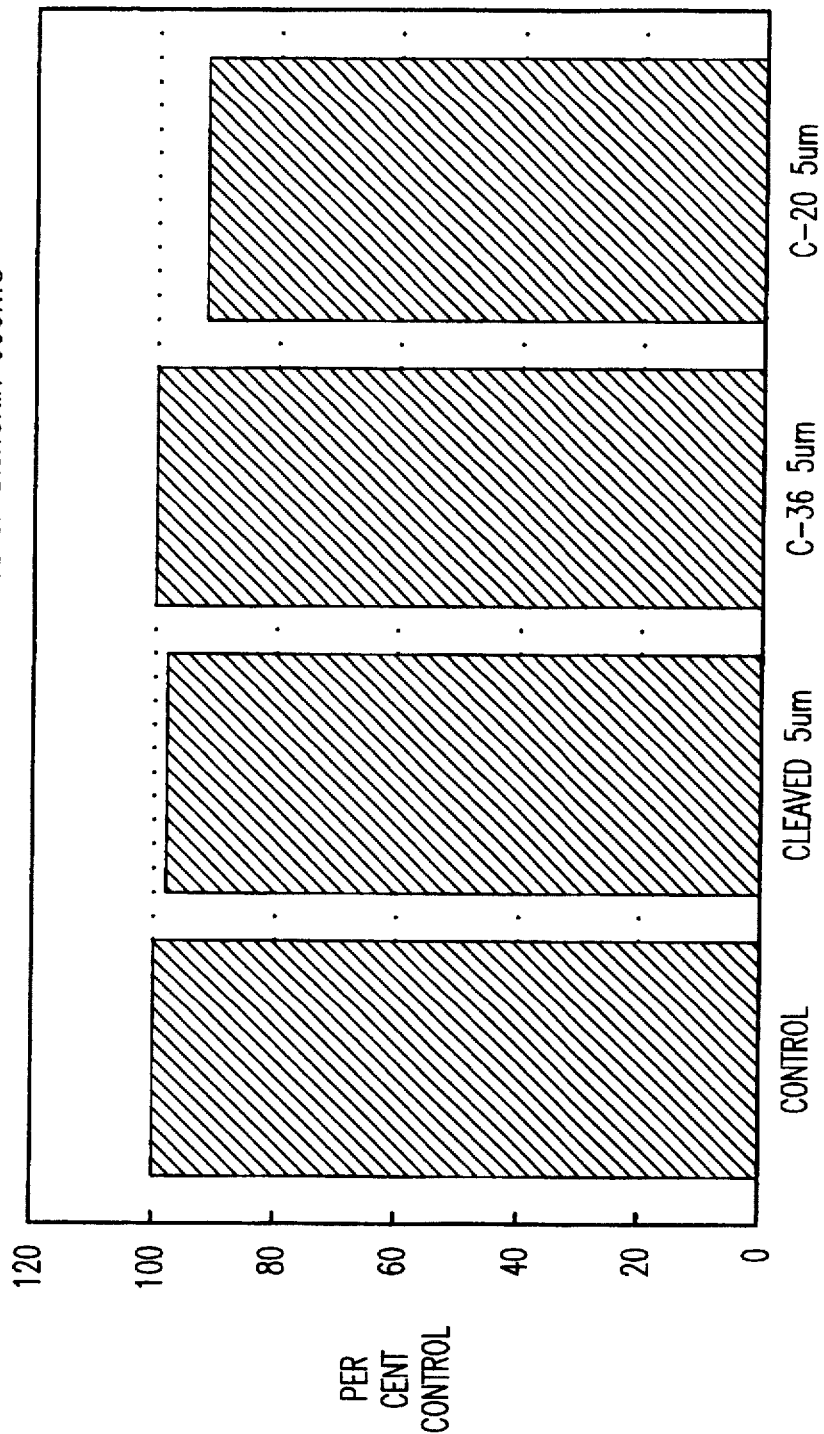

METHOD AND COMPOSITION FOR LOWERING LOW DENSITY LIPOPROTEIN CHOLESTEROL

BACKGROUND OF THE INVENTION

1. Field of the Invention

The invention relates generally to methods and compositions used for lowering low density lipoprotein (LDL) cholesterol levels in patients and, more particularly, to the new use of a naturally occurring protein and fragments and derivatives thereof for lowering LDL cholesterol in the treatment of a wide variety of disorders including atherosclerosis, hypercholesterolemia, gallstones, etc.

2. Description of the Prior Art

Choleseterol is a monohydric secondary alcohol of the cyclopenenophenanthrene (4-ring fused) system, and is the most abundant sterol in humans and higher animals. It is found in all body tissues, especially the brain, spinal cord, and in animal fats or oils, and is the main constituent of gallstones. The human body utilizes cholesterol as the precursor of bile acids, steroid hormones, and provitamin $D_3$. Cholesterol is present in the body in part as a free sterol and in part esterified with higher fatty acids as a lipid in human blood serum.

High levels of serum cholesterol bound to low density lipoprotein, commonly referred to as "LDL cholesterol", is known to correlate strongly with the occurrence of atherosclerosis in humans. Pharmacological methods for lowering serum cholesterol levels currently employ small molecule inhibitors of specific enzymes of the cholesterol biosynthetic pathway. Proprietary drugs for the treatment of hypercholesterolemia (e.g., Mevacor® and Gemfibrozil®) are generally effective, but do have some side effects. Since cholesterol homeostasis is critical, perturbations to cholesterol levels can have profound consequences in some patients, particularly those with liver pathologies. Other side effects disqualify existing medications for some patients with hypercholesterolemia.

SUMMARY OF THE INVENTION

It is an object of this invention to provide a method and composition for lowering LDL cholesterol in human and animal patients.

According to the invention, $\alpha_1$-antitrypsin and cleaved peptide fragments thereof have been found to upregulate the LDL receptor levels in the liver. By providing a patient with $\alpha_1$-antitrypsin or certain cleaved peptide fragments thereof, the patient's level of circulating LDL cholesterol will be reduced due to the increased level of LDL cholesterol receptors in the liver cells, increased bile acid synthesis, and other changes in cholesterol metabolism.

BRIEF DESCRIPTION OF THE DRAWINGS

The foregoing and other objects, aspects and advantages will be better understood from the following detailed description of the preferred embodiments of the invention with reference to the drawings, in which:

FIGS. 1a–b are bar graphs showing LDL binding in human HepG2 cells and rat hepatocytes, respectively;

FIGS. 4a–b are bar graphs showing changes in acetate conversion in human HepG2 and rat hepatocytes, respectively, as a measure of cholesterol biosynthesis.

Figure 1B:
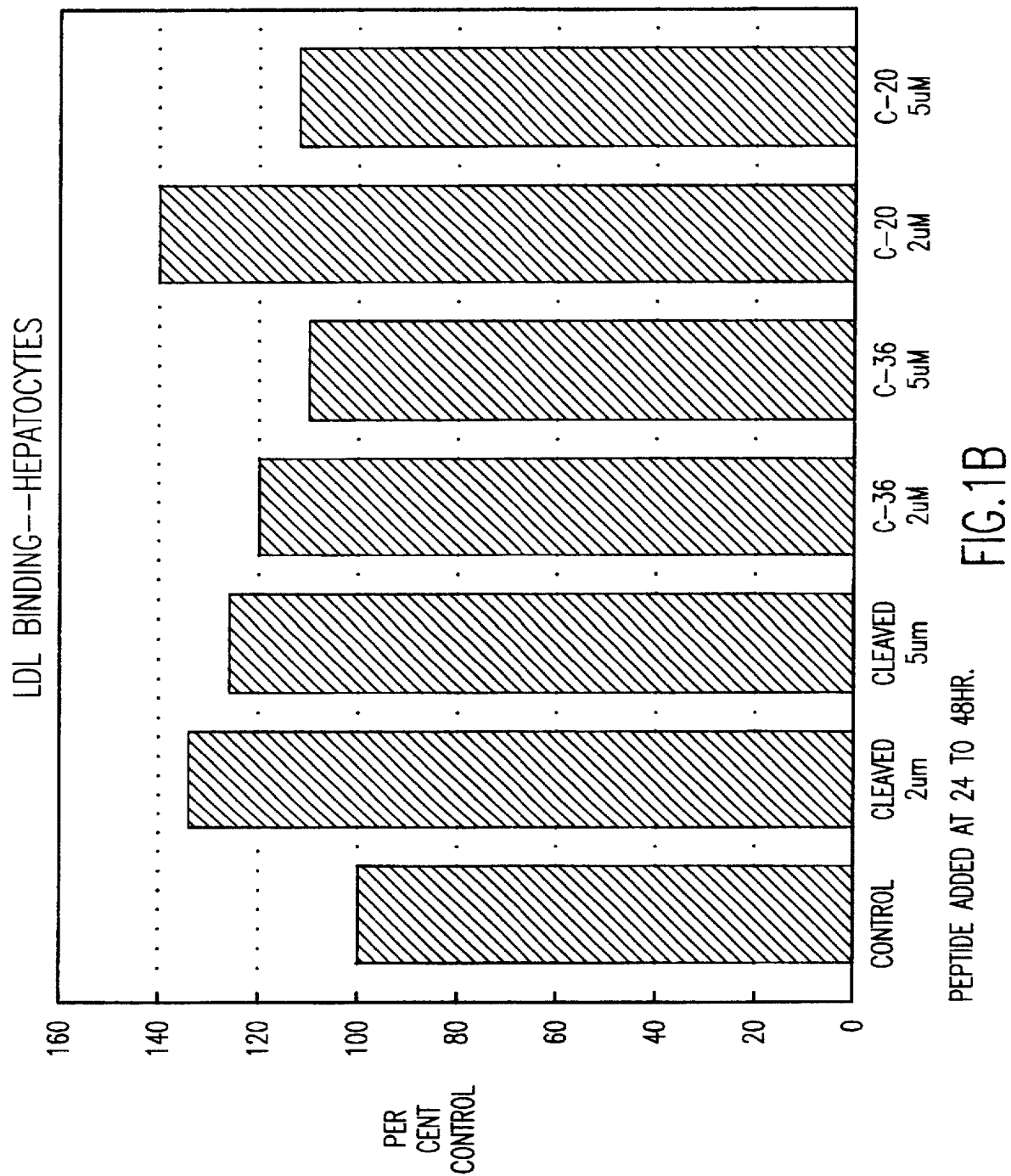

DETAILED DESCRIPTION OF THE PREFERRED EMBODIMENTS OF THE INVENTION $\alpha_1$-antitrypsin is a glycoprotein that is the major serine protease inhibitor (serpin) of human serum. $\alpha_1$-antitrypsin is synthesized in the liver and is genetically polymorphic due to the presence of over twenty alleles. The compound is comprised of 394 amino acid residues and 3 carbohydrate side chains linked to asparagine residues, and is primarily used by the body to inhibit serine proteases, including neutrophil and leukocyte elastase, which degrade connective tissue. $\alpha_1$-antitrypsin has also been used therapeutically in the treatment of emphysema (Merck Index, $11^{th}$ ed., entry 751 at pg 114).

It has been observed that upon interaction with leukocyte elastase and other proteases, a peptide bond is cleaved in the $\alpha_1$-antitrypsin, changing its tertiary structure and rendering it inactive as an inhibitor. The population of cleaved $\alpha_1$-antitrypsin molecules is cleared from the circulation through receptors in the liver. The uptake of cleaved $\alpha_1$-antitrypsin molecules and/or the carboxyl terminal peptide of cleaved $\alpha_1$-antitrypsin by liver cells is especially high during conditions of inflammation and in the acute phase. These conditions are accompanied by hypocholesterolemia. It has been found that exogenous $\alpha_1$-antitrypsin, and fragments and derivatives thereof, can be used to increase the uptake of LDL cholesterol by cultured liver cells. The cause of this depletion of extracellular cholesterol is due to an increase in the number of LDL receptors in liver cells which take up the LDL-cholesterol complex, and to an increase in bile acid synthesis which is a metabolic pathway for excretion of cholesterol derivatives.

This invention takes advantage of the fact that there is an increase in LDL receptor levels and bile acid synthesis induced by the cleaved $\alpha_1$-antitrypsin without any accompanying increase in cellular cholesterol biosynthesis. Specifically, extracellular levels of LDL cholesterol can be reduced by providing the patient with a sufficient quantity of additional $\alpha_1$-antitrypsin or fragments or derivatives thereof. The cleaved $\alpha_1$-antitrypsin or its substituent peptides resulting from interaction with leukocyte elastase are taken up by receptors in the liver and result in increased clearance of LDL-bound cholesterol through these receptors, and thereby decreases circulating levels of LDL.

The forms of $\alpha_1$-antitrypsin with hypocholesterolemic activity include $\alpha_1$-antitrypsin (in the presence of proteases which cleave it at residue 358), $\alpha_1$-antitrypsin proteolytically cleaved at amino acid residue 358, a carboxyl terminal peptide of $\alpha_1$-antitrypsin after cleaving at amino acid residue 358 identified as Sequence ID No. 1, as well as sub-peptides of the carboxyl terminal peptide Sequence ID No. 1, including the twenty amino acid sub-peptide having Sequence ID NO.2. Peptides which are related to SEQ ID No. 1 may also be active, and these peptides are defined by Sequence ID Nos. 3–15.

SEQ 1:  Ser Ile Pro Pro Glu Val Lys Phe Asn Lys Pro Phe Val Phe Leu Met Ile
        Glu Gln Asn Thr Lys Ser Pro Leu Phe Met Gly Lys Val Val Asn Pro Thr
        Gln Lys

SEQ 2:  Ile Glu Gln Asn Thr Lys Ser Pro Leu Phe Met Gly Lys Val Val Asn Pro
        Thr Gln Lys

SEQ 3: Ser Thr Gln Val Arg Phe Thr Val Asp Arg Pro Phe Leu Phe Leu Ile Tyr
Glu His Arg Thr Ser Cys Leu Leu Phe Met Gly Arg Val Ala Asn Pro Ser
Arg Ser

SEQ 4: Ser Leu Asn Pro Asn Arg Val Thr Phe Lys Ala Asn Arg Pro Phe Leu Val
Phe Ile Arg Glu Val Pro Leu Asn Thr Ile Ile Phe Met Gly Arg Val Ala
Asn Pro Cys Val Lys

SEQ 5: Thr Leu Leu Val Phe Glu Val Gln Gln Pro Phe Leu Phe Val Leu Trp Asp
Gln Gln His Lys Phe Pro Val Phe Met Gly Arg Val Tyr Asp Pro Arg Ala

SEQ 6: Met Ala Pro Glu Glu Ile Ile Met Asp Arg Pro Phe Leu Phe Val Val Arg
His Asn Pro Thr Gly Thr Val Leu Phe Met Gly Gln Val Met Glu Pro

SEQ 7: Pro Glu Asn Thr Phe Leu His Pro Ile Ile Gln Ile Asp Arg Ser Phe Met
Leu Leu Ile Leu Glu Arg Ser Thr Arg Ser Ile Leu Phe Leu Gly Lys Val
Val Asn Pro Thr Glu Ala

SEQ 8: Ser Ala Leu Val Glu Thr Arg Thr Ile Val Arg Phe Asn Arg Pro Phe Leu
Met Ile Ile Val Pro Thr Asp Thr Gln Asn Ile Phe Phe Met Ser Lys Val
Thr Asn Pro Lys Gln Ala

SEQ 9: Met Ser Leu Ser Ser Phe Ser Val Asn Arg Pro Phe Leu Phe Phe Ile Phe
Glu Asp Thr Thr Gly Leu Pro Leu Phe Val Gly Ser Val Arg Asn Pro Asn
Pro Ser Ala Pro Arg Glu Leu

SEQ 10: Ser Val Ser Glu Glu Phe Arg Ala Asp His Pro Phe Leu Phe Cys Ile Lys
His Ile Ala Thr Asn Ala Val Leu Phe Phe Gly Arg Cys Val Ser Pro

SEQ 11: Thr Gly His Gly Gly Pro Gln Phe Val Ala Asp His Pro Phe Leu Phe Leu
Ile Met His Lys Ile Thr Lys Cys Ile Leu Phe Phe Gly Arg Phe Cys Ser Pro

SEQ 12: Glu Val Leu Glu Val Thr Leu Asn Arg Pro Phe Leu Phe Ala Val Tyr Asp
Gln Ser Ala Thr Ala Leu His Phe Leu Gly Arg Val Ala Asn Pro Leu Ser
Thr Ala

SEQ 13: Ser Lys Pro Ile Ile Leu Arg Phe Asn Gln Pro Phe Ile Ile Met Ile Phe
Asp His Phe Thr Trp Ser Ser Leu Phe Leu Ala Arg Val Met Asn Pro Val

SEQ 14: Ser Ala Arg Leu Asn Ser Gln Arg Leu Val Phe Asn Arg Pro Phe Leu Met
Phe Ile Val Asp Asn Asn Ile Leu Phe Leu Gly Lys Val Asn Arg Pro

-continued

SEQ 15: Ser Ser Pro Pro Trp Phe Ile Val Asp Arg Pro Phe Leu Phe Phe Ile Arg

His Asn Pro Thr Gly Ala Val Leu Phe Met Gly Gln Ile Asn Lys Pro

The peptide fragments of α₁-antitrypsin can be referred to as hypocholesterolemic peptides because, like α₁-antitrypsin, they increase LDL receptor levels in liver cells, and increase bile acid synthesis, without any accompanying increase in cellular cholesterol biosynthesis. They are distinct from currently used cholesterol lowering compounds mentioned above in not affecting cholesterol biosynthesis.

Thus, a patient can be provided with either α₁-antitrypsin, or its hypocholesterolemic peptides, in order to reduce circulating LDL cholesterol by increasing LDL cholesterol receptor sites and increasing bile acid synthesis in liver cells. The carboxyl terminal peptide (SEQ ID No. 1) or fragments thereof (e.g., SEQ ID No. 2), or related peptides (SEQ ID Nos. 3–15) may be preferred for use in the practice of this invention since they are low molecular weight compounds that can up-regulate LDL receptor levels and increase bile acid synthesis, and should be more easily delivered to and used by the patient; however, if a hypocholesterolemic peptide is chosen, it will need to be stable and active in vivo.

α₁-antitrypsin can be purified from human serum or in non-glycosylated form from recombinant plasmids in bacterial cells carrying the gene for the protein according to methods known to one of ordinary skill in the art. The hypocholesterolemic peptides can be obtained by proteinase treatment of uncleaved α₁-antitrypsin. The α₁-antitrypsin or hypocholesterolemic peptides would preferably be provided to a patient by infusion, implant or slow delivery vehicle to establish micromolar concentrations. However, other methods of delivery including intraperitoneal, intravenous, sublingual, oral, and the like may be useful with the practice of this invention, and the α₁-antitrypsin or hypocholesterolemic peptides may be combined with a wide variety of compounds depending on the mode of delivery including saline, water, oils, emulsions, propellants (e.g., CFCs and HFCs), preservatives (e.g., BAK, parabens), binders (e.g., lactose), elixirs, syrups, etc. The dose provided should be sufficient to decrease circulating levels of LDL, and to increase LDL receptor levels and bile acid synthesis in the liver. The dose may vary widely depending on the mode of delivery, the age and gender of the patient, and the patient's previous medical history.

The treatment methodology of this invention should avoid immune side effects because a naturally occurring human serum protein is being used and because the invention involves amplifying a natural regulatory circuit. It is novel and distinct from pharmacological agents currently in use to lower serum cholesterol levels in that it does not act either directly as an inhibitor of, or indirectly, by decreasing cholesterol biosynthesis.

EXAMPLE

α₁-antitrypsin and its hypocholesterolemic peptides (SEQ ID No. 1 and SEQ ID No. 2) have been tested experimentally on several parameters of cholesterol status in human HepG2 cells (a transformed cell line) and in rat hepatocytes (a normal, but non-human line of liver cells). The results summarized below demonstrate a cross-species reactivity which points to the generality of the effect and is consistent with the high sequence similarity between the rat and human hypocholesterolemic peptides. In the results below, proteolytically cleaved α₁-antitrypsin is identified as "cleaved", the carboxyl terminal sequence SEQ 1 is identified as "C-36", and the subpeptide fragment SEQ 2 is identified as "C-20".

With reference to FIG. 1, an experiment was conducted wherein iodine labeled LDL was incubated with HepG2 or rat hepatocytes in culture with and without cleaved α₁-antitrypsin or hypocholesterolemic peptides. The cleaved α₁-antitrypsin and hypocholesterolemic peptides were added 24–48 hr after incubation began in 2 micromolar (µM) or 5µM concentrations. The bound LDL was quantitated by counting. The control indicates the amount of bound LDL obtained when no cleaved α₁-antitrypsin or hypocholesterolemic peptides are present. FIG. 1 shows maximum LDL binding occurs when 2µM α₁-antitrypsin or its peptide derivatives are added.

Figure 2:
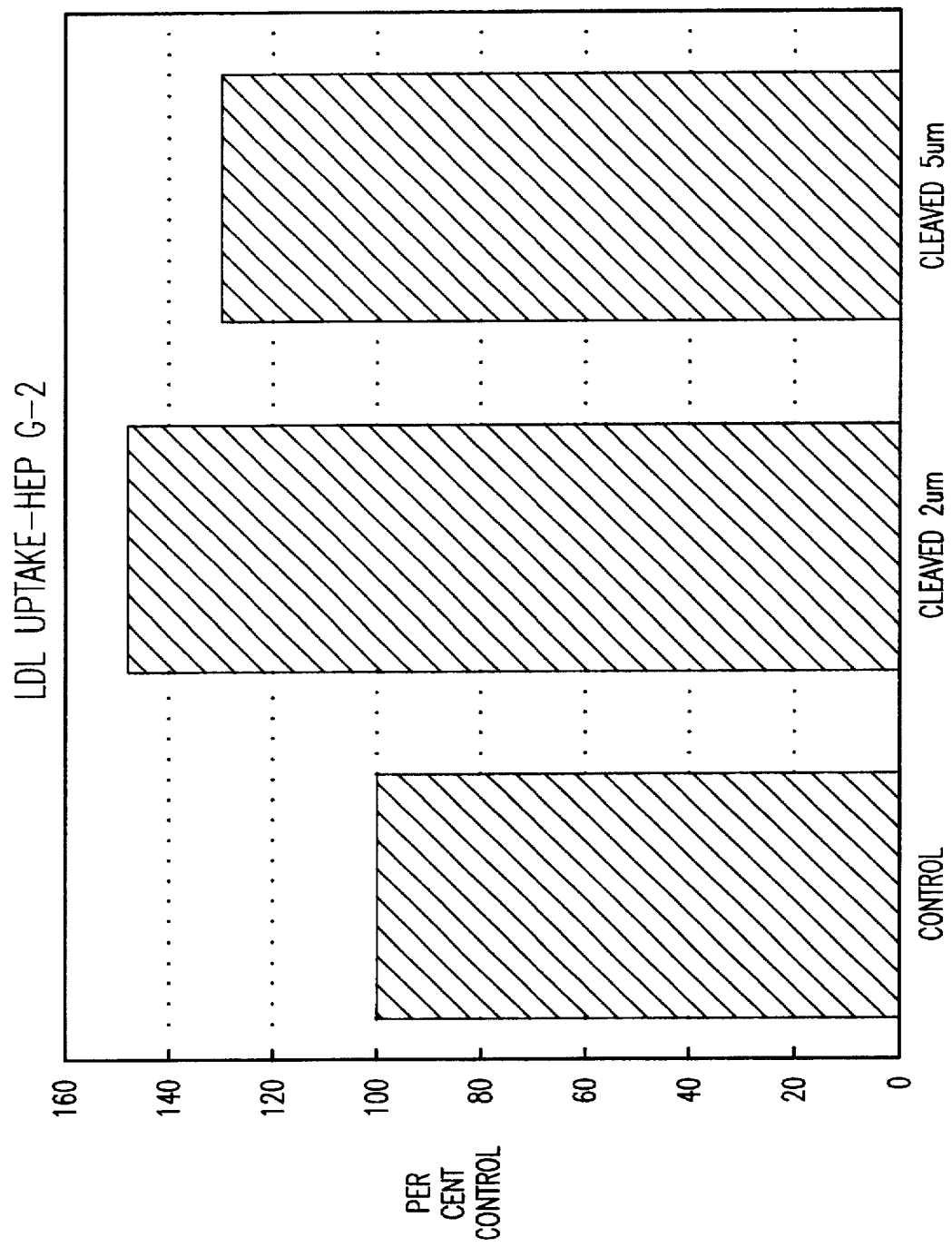
FIG. 2 is a bar graph showing LDL uptake in human HepG2 cells.

FIG. 2 shows internalized counts of LDL in HepG2 cells. FIG. 2 shows that LDL is taken up in response to the cleaved α₁-antitrypsin and hypocholesterolemic peptides. This demonstrates that the increased number of LDL receptors induced by α₁-antitrypsin and hypocholesterolemic peptides (FIGS. 1a–b) are competent to remove LDL from the external milieu (hepatic circulation, in vivo) to the cell cytosol, where further metabolic conversions occur.

Figure 3A:
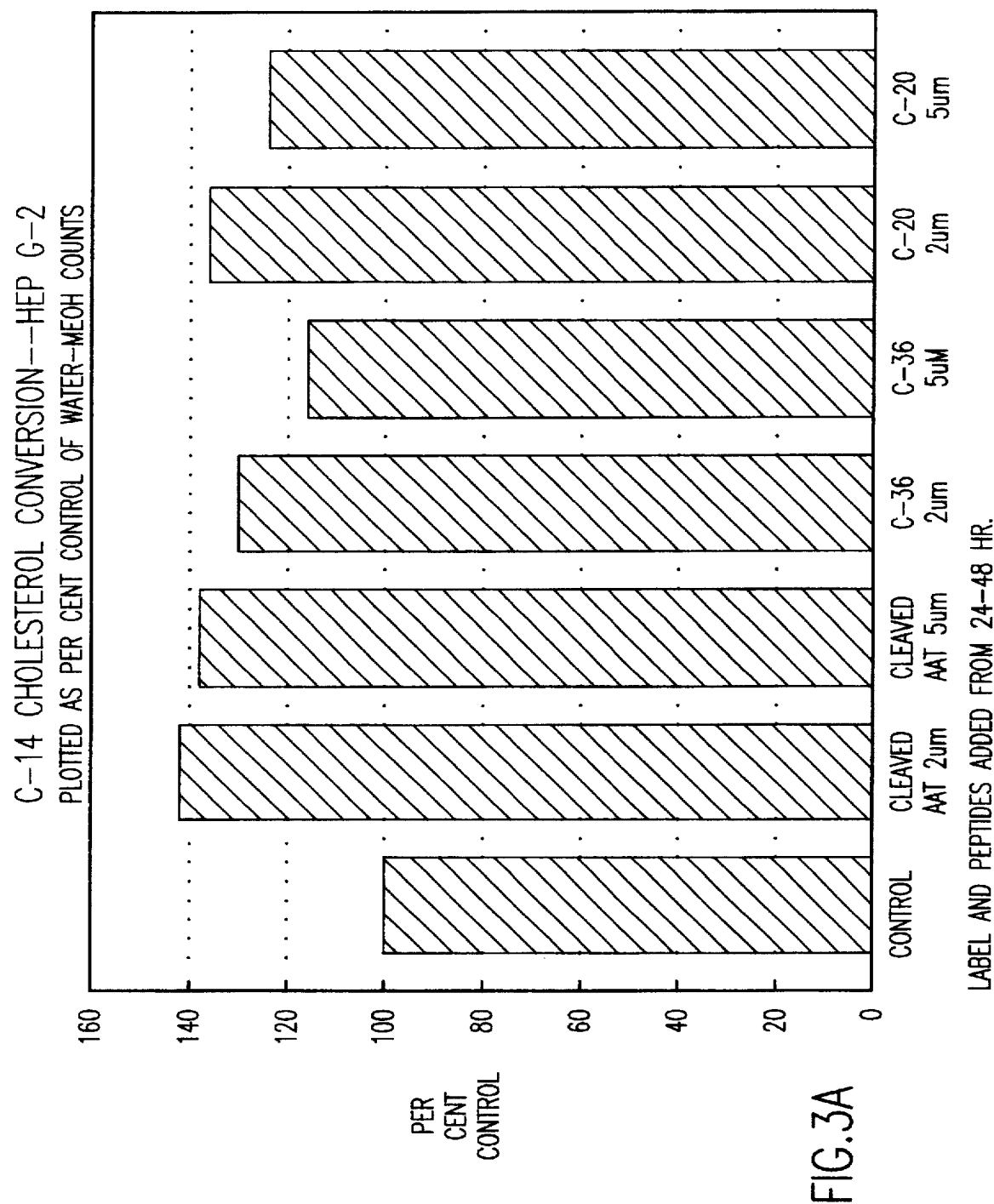
FIGS. 3a–b are bar graphs showing conversion of labeled cholesterol to bile acids in human HepG2 cells and rat hepatocytes, respectively.
Figure 3B:
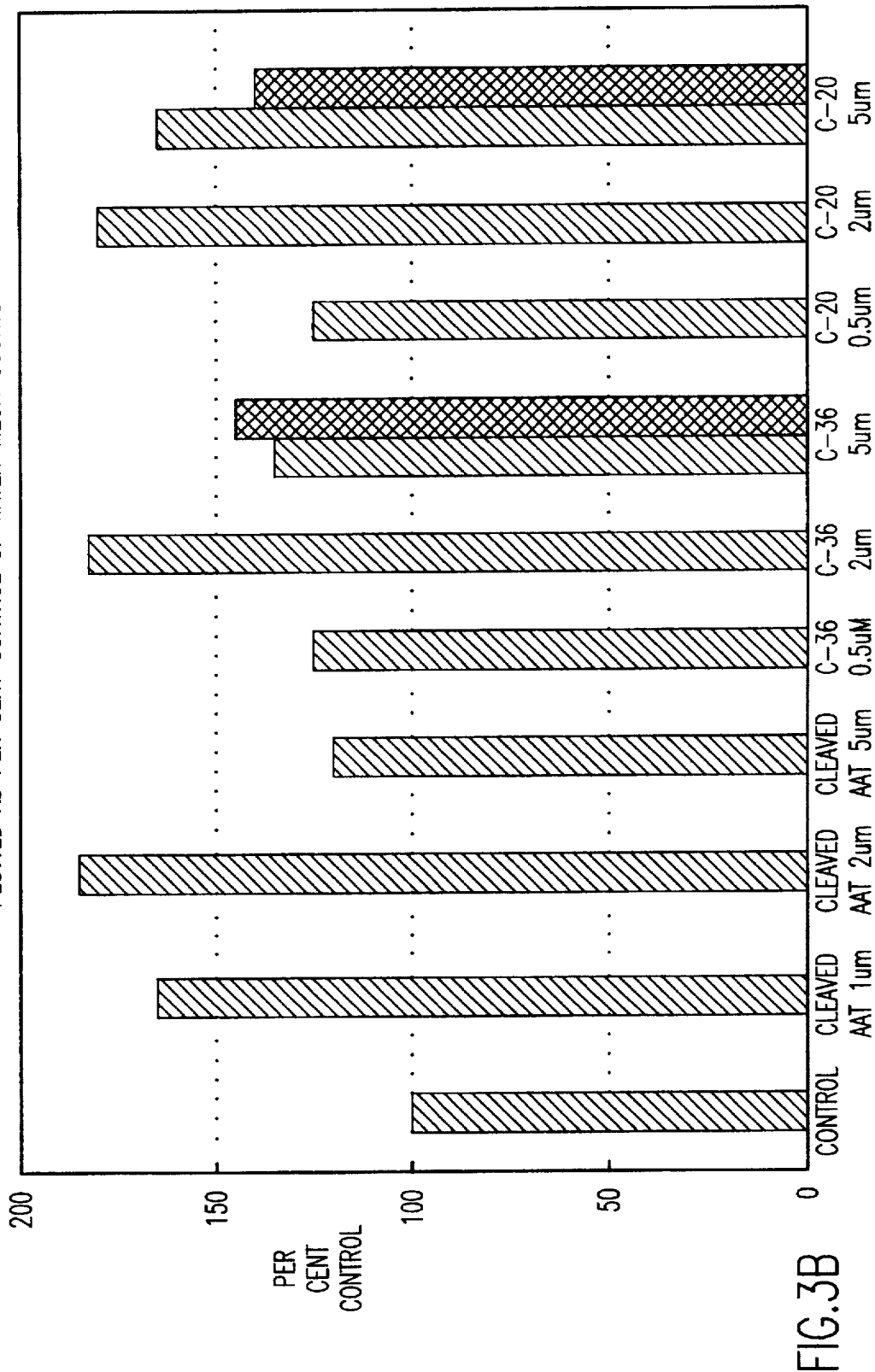

FIGS. 3a–b show the conversion of carbon 14 labeled cholesterol to bile acids. Bile acids are solubilized cholesterol which is mostly excreted. Thus, conversion to bile acids represents a decrease in cholesterol. The labeled cholesterol and peptides were added 24–48 hours after the beginning of the incubation period of HepG2 cells or rat hepatocytes. The results are plotted as the percent of control (no cleaved α₁-antitrypsin or hypocholesterolemic peptides added to control) in water-methanol counts. In FIG. 3b, different stipled bars represent experiments performed on different days. FIGS. 3a–b show that cleaved α₁-antitrypsin and hypocholesterolemic peptides stimulate bile acid synthesis.

Figure 4B:
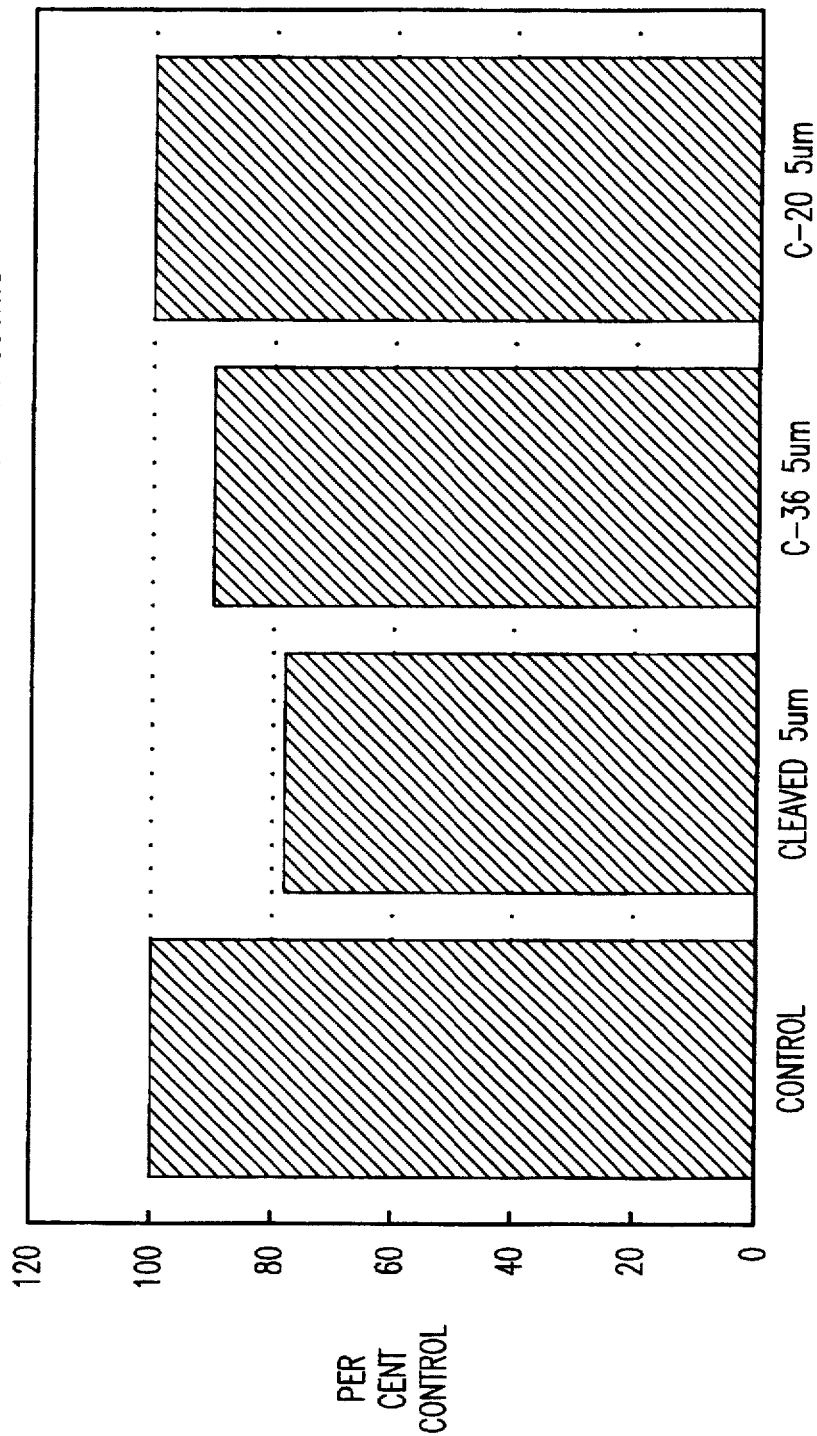

FIGS. 4a–b show the effects of α₁-antitrypsin and hypocholesterolemic peptides on de novo cholesterol biosynthesis being monitored by using ⁴C-labeled precursor acetate and extracting newly synthesized, labeled cholesterol with digitonin for counting. FIGS. 4a–b provide a measure of the changes in cholesterol biosynthesis, and demonstrate there is no up-regulation of cholesterol biosynthesis even though bile acid synthesis increases.

The results in FIGS. 1–4 indicate that cleaved α₁-antitrypsin and hypocholesterolemic peptides can be used to decrease circulating LDL cholesterol by increasing LDL binding and uptake due to increased LDL binding sites, and by up-regulating bile acid synthesis which leads to cholesterol excretion, and that cholesterol homeostasis is broken in that there is no compensating up-regulation of de novo cholesterol synthesis.

While the invention has been described in terms of its preferred embodiments, those skilled in the art will recognize that the invention can be practiced with modification within the spirit and scope of the appended claims.

I claim:

1. A method for lowering low density lipoprotein cholesterol in a patient in need thereof, comprising the step of administering to said patient a sufficient quantity of a compound selected from the group consisting of $\alpha_1$-antitrypsin, a $\alpha_1$-antitrypsin an amino of carboxyl terminal peptide of proteolytically cleaved at amino acid residue 358 and peptides as defined by SEQ ID No. 2–15 to increase low density lipoprotein cholesterol receptors and bile acid synthesis in liver cells without increasing cellular cholesterol synthesis in said patient.

2. The method of claim 1 wherein said compound is $\alpha_1$-antitrypsin.

3. The method of claim 1 wherein said compound is $\alpha_1$-antitrypsin cleaved at amino acid residue 358.

4. The method of claim 1 wherein said compound is SEQ ID No. 1.

5. The method of claim 1 wherein said compound is SEQ ID No. 2.

6. The method of claim 1 wherein said compound is selected from the group defined by SEQ ID No. 3–15.

* * * * *

UNITED STATES PATENT AND TRADEMARK OFFICE
CERTIFICATE OF CORRECTION

PATENT NO. : 5,792,749
DATED : August 11, 1998
INVENTOR(S) : Wright

It is certified that error appears in the above-identified patent and that said Letters Patent is hereby corrected as shown below:

In the claims, claim 1, lines 5 and 6, replace "a alpha-1 antitrypsin an amino of carboxyl terminal peptide of"

with --an amino or carboxyl terminal peptide of alpha 1-antitrypsin--

Signed and Sealed this

Twenty-ninth Day of June, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
    ( A ) LENGTH: 36 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:1:

Ser Ile Pro Pro Glu Val Lys Phe Asn Lys Pro Phe Val Phe Leu Met
  1               5                   10                  15

Ile Glu Gln Asn Thr Lys Ser Pro Leu Phe Met Gly Lys Val Val Asn
                  20                  25                  30

Pro Thr Gln Lys
              35

( 2 ) INFORMATION FOR SEQ ID NO:2:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:2:

Ile Glu Gln Asn Thr Lys Ser Pro Leu Phe Met Gly Lys Val Val Asn
  1               5                   10                  15

Pro Thr Gln Lys
              20

( 2 ) INFORMATION FOR SEQ ID NO:3:

( i ) SEQUENCE CHARACTERISTICS:
    ( A ) LENGTH: 36 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:3:

Ser Thr Gln Val Arg Phe Thr Val Asp Arg Pro Phe Leu Phe Leu Ile
  1               5                   10                  15

Tyr Glu His Arg Thr Ser Cys Leu Leu Phe Met Gly Arg Val Ala Asn
                  20                  25                  30

Pro Ser Arg Ser
              35

( 2 ) INFORMATION FOR SEQ ID NO:4:

( i ) SEQUENCE CHARACTERISTICS:
    ( A ) LENGTH: 39 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:4:

Ser Leu Asn Pro Asn Arg Val Thr Phe Lys Ala Asn Arg Pro Phe Leu
1               5                   10                  15

Val Phe Ile Arg Glu Val Pro Leu Asn Thr Ile Ile Phe Met Gly Arg
            20                  25                  30

Val Ala Asn Pro Cys Val Lys
            35

( 2 ) INFORMATION FOR SEQ ID NO:5:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Thr Leu Leu Val Phe Glu Val Gln Gln Pro Phe Leu Phe Val Leu Trp
1               5                   10                  15

Asp Gln Gln His Lys Phe Pro Val Phe Met Gly Arg Val Tyr Asp Pro
            20                  25                  30

Arg Ala ( 2 ) INFORMATION FOR SEQ ID NO:6:

( i ) SEQUENCE CHARACTERISTICS:
        ( A ) LENGTH: 33 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

Met Ala Pro Glu Glu Ile Ile Met Asp Arg Pro Phe Leu Phe Val Val
1               5                   10                  15

Arg His Asn Pro Thr Gly Thr Val Leu Phe Met Gly Gln Val Met Glu
            20                  25                  30

Pro ( 2 ) INFORMATION FOR SEQ ID NO:7:

( i ) SEQUENCE CHARACTERISTICS:
        ( A ) LENGTH: 40 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

Pro Glu Asn Thr Phe Leu His Pro Ile Ile Gln Ile Asp Arg Ser Phe
1               5                   10                  15

Met Leu Leu Ile Leu Glu Arg Ser Thr Arg Ser Ile Leu Phe Leu Gly
            20                  25                  30

Lys Val Val Asn Pro Thr Glu Ala
            35                  40

( 2 ) INFORMATION FOR SEQ ID NO:8:

( i ) SEQUENCE CHARACTERISTICS:

(A) LENGTH: 40 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:8:

```
Ser Ala Leu Val Glu Thr Arg Thr Ile Val Arg Phe Asn Arg Pro Phe
 1               5                  10                  15
Leu Met Ile Ile Val Pro Thr Asp Thr Gln Asn Ile Phe Phe Met Ser
                20                  25                  30
Lys Val Thr Asn Pro Lys Gln Ala
                35                  40
```

(2) INFORMATION FOR SEQ ID NO:9:

(i) SEQUENCE CHARACTERISTICS:
    (A) LENGTH: 41 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:9:

```
Met Ser Leu Ser Ser Phe Ser Val Asn Arg Pro Phe Leu Phe Phe Ile
 1               5                  10                  15
Phe Glu Asp Thr Thr Gly Leu Pro Leu Phe Val Gly Ser Val Arg Asn
                20                  25                  30
Pro Asn Pro Ser Ala Pro Arg Glu Leu
                35                  40
```

(2) INFORMATION FOR SEQ ID NO:10:

(i) SEQUENCE CHARACTERISTICS:
    (A) LENGTH: 33 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:10:

```
Ser Val Ser Glu Glu Phe Arg Ala Asp His Pro Phe Leu Phe Cys Ile
 1               5                  10                  15
Lys His Ile Ala Thr Asn Ala Val Leu Phe Phe Gly Arg Cys Val Ser
                20                  25                  30
Pro
```

(2) INFORMATION FOR SEQ ID NO:11:

(i) SEQUENCE CHARACTERISTICS:
    (A) LENGTH: 35 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:11:

```
Thr Gly His Gly Gly Pro Gln Phe Val Ala Asp His Pro Phe Leu Phe
 1               5                  10                  15
Leu Ile Met His Lys Ile Thr Lys Cys Ile Leu Phe Phe Gly Arg Phe
                20                  25                  30
```

```
        Cys  Ser  Pro
                  35
```

( 2 ) INFORMATION FOR SEQ ID NO:12:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

```
Glu  Val  Leu  Gly  Val  Thr  Leu  Asn  Arg  Pro  Phe  Leu  Phe  Ala  Val  Tyr
 1                   5                        10                       15

Asp  Gln  Ser  Ala  Thr  Ala  Leu  His  Phe  Leu  Gly  Arg  Val  Ala  Asn  Pro
                20                       25                       30

Leu  Ser  Thr  Ala
               35
```

( 2 ) INFORMATION FOR SEQ ID NO:13:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

```
Ser  Lys  Pro  Ile  Ile  Leu  Arg  Phe  Asn  Gln  Pro  Phe  Ile  Ile  Met  Ile
 1                   5                        10                       15

Phe  Asp  His  Phe  Thr  Trp  Ser  Ser  Leu  Phe  Leu  Ala  Arg  Val  Met  Asn
                20                       25                       30

Pro  Val
```

( 2 ) INFORMATION FOR SEQ ID NO:14:

( i ) SEQUENCE CHARACTERISTICS:
        ( A ) LENGTH: 33 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

```
Ser  Ala  Arg  Leu  Asn  Ser  Gln  Arg  Leu  Val  Phe  Asn  Arg  Pro  Phe  Leu
 1                   5                        10                       15

Met  Phe  Ile  Val  Asp  Asn  Asn  Ile  Leu  Phe  Leu  Gly  Lys  Val  Asn  Arg
                20                       25                       30

Pro
```

( 2 ) INFORMATION FOR SEQ ID NO:15:

( i ) SEQUENCE CHARACTERISTICS:
        ( A ) LENGTH: 33 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

-continued

| Ser | Ser | Pro | Pro | Trp | Phe | Ile | Val | Asp | Arg | Pro | Phe | Leu | Phe | Phe | Ile |
|---|---|---|---|---|---|---|---|---|---|---|---|---|---|---|---|
| 1 | | | | 5 | | | | | 10 | | | | | 15 | |
| Arg | His | Asn | Pro | Thr | Gly | Ala | Val | Leu | Phe | Met | Gly | Gln | Ile | Asn | Lys |
| | | | 20 | | | | | 25 | | | | | 30 | | |
| Pro | | | | | | | | | | | | | | | |